(12) United States Patent
Robotti et al.

(10) Patent No.: US 8,178,046 B2
(45) Date of Patent: May 15, 2012

(54) MICROFLUIDIC DEVICES WITH SPR SENSING CAPABILITIES

(75) Inventors: Karla Robotti, Mountain View, CA (US); Daniel B. Roitman, Menlo Park, CA (US); Kevin Killeen, Palo Alto, CA (US)

(73) Assignee: Sierra Sensors GmbH, Hamburg (DE)

( * ) Notice: Subject to any disclaimer, the term of this patent is extended or adjusted under 35 U.S.C. 154(b) by 2363 days.

(21) Appl. No.: 11/064,575

(22) Filed: Feb. 23, 2005

(65) Prior Publication Data
US 2006/0188401 A1 Aug. 24, 2006

(51) Int. Cl.
*G01N 33/553* (2006.01)

(52) U.S. Cl. .................. 422/82.05; 422/82.09; 436/525; 356/445; 257/431

(58) Field of Classification Search ........................ None
See application file for complete search history.

(56) References Cited

U.S. PATENT DOCUMENTS

| | | | |
|---|---|---|---|
| 5,395,587 A | 3/1995 | Brigham-Burke et al. | |
| 5,443,890 A | 8/1995 | Ohman | |
| 5,500,071 A | 3/1996 | Kaltenbach et al. | |
| 5,561,069 A | 10/1996 | Brigham-Burke et al. | |
| 5,644,069 A | 7/1997 | Liu et al. | |
| 5,658,413 A | 8/1997 | Kaltenbach et al. | |
| 5,962,081 A | 10/1999 | Ohman et al. | |
| 6,008,893 A | 12/1999 | Roos et al. | |
| 6,033,628 A | 3/2000 | Kaltenbach et al. | |
| 6,066,448 A | 5/2000 | Wohlstadter et al. | |
| 6,127,129 A | 10/2000 | Corn et al. | |
| 6,300,141 B1 | 10/2001 | Segal et al. | |
| 6,331,276 B1 * | 12/2001 | Takei et al. | 422/82.09 |
| 6,361,958 B1 | 3/2002 | Shieh et al. | |
| 6,415,235 B1 * | 7/2002 | Bartholomew et al. | 702/28 |
| 6,493,090 B1 | 12/2002 | Lading et al. | |
| 6,524,790 B1 | 2/2003 | Kopf-Sill et al. | |
| 2001/0030751 A1 * | 10/2001 | Bartholomew et al. | 356/445 |
| 2002/0128593 A1 | 9/2002 | Sjolander et al. | |
| 2002/0135772 A1 | 9/2002 | Bornhop et al. | |
| 2002/0187557 A1 | 12/2002 | Hobbs et al. | |
| 2003/0017579 A1 | 1/2003 | Corn et al. | |
| 2004/0046963 A1 * | 3/2004 | Lackritz et al. | 356/445 |
| 2004/0080744 A1 | 4/2004 | Hobbs | |
| 2004/0155309 A1 * | 8/2004 | Sorin et al. | 257/433 |
| 2005/0117158 A1 * | 6/2005 | Kanai et al. | 356/445 |
| 2005/0248758 A1 * | 11/2005 | Carron et al. | 356/301 |
| 2007/0184456 A1 * | 8/2007 | Chee et al. | 435/6 |

OTHER PUBLICATIONS

Klaus B. Mogensen, Peter Friis, Jorg Hubner, Nikolaj Petersen, Anders M. Jorgensen, Pieter Telleman, and Jorg P. Kutter, "Ultraviolet transparent silicon oxynitrade waveguides for biochemical microsystems", 2001 Optical Society of America, Optics Letters vol. 26, No. 10, May 15, 2001, pp. 716-718.

Yasuko Yamada Maruo, Sigekuni Sasaki, and Toshiaki Tamamura, "Embedded channel polyimide waveguide fabrication by direct electron beam writing method", Journal of Lightwave Technology, vol. 13 Aug. 1995, No. 8 New York, NY, US, pp. 1718-1723.

EP Search Report 06000 2090 dated Apr. 28, 2006. Nelson et al., "Near-Infrared Surface Plasmon Resonance Measurements of Ultrathin Films. 1. Angle Shift and SPR Imaging Experiments," Analytical Chemistry 1999, 71, 3928-3934.

EP Application No. 06002090.6 filed Feb. 1, 2006. Office Action dated May 23, 2008.

* cited by examiner

*Primary Examiner* — In Suk Bullock
*Assistant Examiner* — Timothy G Kingan
(74) *Attorney, Agent, or Firm* — Boyle Fredrickson S.C.

(57) ABSTRACT

A microfluidic system including a chip sensor and an SPR optical detector. The chip sensor may be made a non-transparent material, such as polyimide or silicon, allowing non-visible radiation produced by the SPR optical detector to pass through and interact with a surface plasmon generating layer on the chip sensor.

26 Claims, 1 Drawing Sheet

MICROFLUIDIC DEVICES WITH SPR SENSING CAPABILITIES

BACKGROUND OF THE INVENTION

1. Field of the Invention

The invention relates to a microfluidic device. More particularly, the invention relates to a non-transparent microfluidic device with surface plasmon resonance ("SPR") capabilities.

2. Description of the Prior Art

The use of conventional SPR as a testing tool offers several advantages. For example, it is relatively fast, it does not require labeling and it can be performed on site. Further, SPR provides for good sensitivity and can be performed in "real time," which generates kinetic information, i.e., one can see the binding while it occurs as opposed to after rinsing off the reagents.

SPR is an optical phenomenon which occurs as a result of total internal reflection of light at a metal film-liquid interface. Total internal reflection is observed in situations where light travels through a medium such as glass, and is reflected back through that medium from the interface with a different medium, for example a liquid buffer solution. In order for total internal reflection to occur, the angle of incidence of the light must be greater than a critical angle determined by the refractive indices of the optical media. Although the light is totally reflected, a component of the incident light momentum, termed the evanescent wave or surface plasmon, penetrates a distance, on the order of one wavelength, into the medium, e.g., the buffer, on the opposite side of the interface.

If the incident light is monochromatic and polarized, and the interface between the media is coated with a thin metal film, such as gold or silver, having a thickness which is a fraction of the wavelength of the incident light, the evanescent wave can interact with free oscillating electrons, or plasmons, in the metal film surface. The plasmons will absorb energy from the evanescent wave at a particular angle of incidence, which is dependent upon the refractive index of the liquid medium adjacent to the metal film, i.e. within a distance of about 300 nm from the metal film. Thus, for a given refractive index in the liquid, the intensity of the reflected light varies according to the angle of incidence of the light, and there is a sharp drop in the intensity of the reflected light at a particular angle at which peak absorbance occurs. This angle can be termed the "resonance angle."

Changes in the refractive index of a buffer solution, for example, will alter the resonance angle. By measuring the angle at which the peak occurs, it is possible to detect changes in the refractive index of the buffer solution. Because proteins, for example, in the buffer solution alter its refractive index, it is possible to measure, and monitor continuously, the protein content in the buffer solution adjacent to the metal film by measuring the resonance angle. Further, the interaction of macromolecules in the buffer solution with, for example, surface immobilized ligand or non-specific binding polymers, e.g., antibody binding to peptide or protein, causes a change in the refractive index. This change results in a correlative change in the resonance angle, which is detectable and quantifiable.

SPR technology is utilized in commercially available instruments, for example, produced by BIACORE (Uppsala, Sweden). Further, a SPR detector is manufactured by Pharmacia Biosensor AB (Uppsala, Sweden).

The BIACORE methodology relies on immobilization of ligands onto the surface of a sensor chip consisting of a glass substrate having a gold film covered by a monolayer of a long hydroxyalkyl thiol to which is covalently attached a thin layer of carboxymethylated dextran. The immobilization procedure is performed with the sensor chip in place in the instrument and is continuously monitored by the SPR detector.

The sensor chip is contacted by a microfluidic cartridge which has formed on it a number of channels which define the flow of samples across the surface of the sensor chip. The microfluidic cartridge, which is in place when the ligand is introduced to the sensor, contains pneumatic valves, which control the flow of samples through the channels.

An unknown sample or ligate solution is introduced into the apparatus to contact the immobilized ligand. The interaction between ligand and ligate is observed directly by surface plasmon resonance techniques and the measurements recorded on a computer via a program such as Bialogue, produced by Pharmacia BioSensor AB. The sensor chip is discarded to waste after interacting with the ligand, however, the microfluidic cartridge is reusable.

The BIACORE system is limited to a glass microfluidic sensor chip given that a transparent material is necessary to allow visible light produced by the BIACORE optical detector to reach the metal film on the sensor chip.

As indicated above, SPR has traditionally been performed with a glass substrate or microfluidic chip. The inventors of the present invention have discovered that SPR may be effectively performed on non-transparent substrates or chips, which offer a number of advantages over glass. Given the above detailed utility of SPR sensing, the expansion of SPR sensing to microfluidic devices made from materials other than transparent glass is highly significant.

Silicon based sensors for measuring radiation reflected off the surface plasmon generating film on a glass substrate are used in some existing SPR systems. Given the heightened sensitivity of silicon sensors at 800 nm, the optical detectors of some SPR systems are configured to generate 800 nm radiation so as to take advantage of this heightened sensor sensitivity. Accordingly, SPR systems, which produce non-visible radiation, i.e., operating in the infra-red region, are known. To date, however, the inventor is not aware of any such SPR system used in combination with a substrate or microfluidic chip made from non-transparent material.

While the prior art microfluidic systems may be suitable for the particular purpose employed, or for general use, they are not as suitable for the purposes of the present invention as disclosed hereafter.

SUMMARY OF THE INVENTION

Accordingly, it is an object of the invention to produce a SPR system that is not limited to use of a transparent glass microfluidic cartridge or chip sensor.

It is a further object of the invention to produce a SPR system, including a non-transparent chip sensor, which allows non-visible radiation produced by an optical detector of the system to at least partially penetrate and generate a surface plasmon in the chip sensor.

The inventors of the present invention have created a SPR system with a microfluidic module designed for the trap and release of analytes using media, such as modified silica-based media. In one exemplary embodiment, the present invention is a microfluidic system comprising a sensor chip and an SPR optical detector. The chip sensor is made from a non-transparent material, for example, such as polyimide or silicon. The sensor chip may be a simple solid substrate with a surface plasmon generating layer on at least a portion of the surface or may include channels at least partially coated with the surface plasmon generating layer. The sensor chip including channels may be molded as a single unit including the channels or made from multiple layers that are laser ablated to form at least one channel. The sensor chip allows for radiation produced by the SPR optical detector to pass through and interact with the surface plasmon generating layer.

Silicon sensor chips are useful because they allow for an integration of electronic circuits with the sensor chip. Further, silicon sensors allow for use of known photolithography and micromachining techniques.

Polyimide sensor chips are useful because they exhibit low sorptive properties towards proteins and peptides, which are known to be particularly difficult to analyze in prior silicon dioxide-based separation systems. Successful demonstrations of separations with this difficult class of solutes typically ensures that separation of other classes of solutes will be not be problematic. Further, since polyimide is a condensation polymer, it is possible to chemically bond groups to the surface, which can provide a variety of desirable surface properties, depending on the target analysis. These bonds to the polymeric substrate demonstrate pH stability in the basic region (pH 9-10).

In an exemplary embodiment of the present invention, the sensor chip may include a solid substrate.

In an exemplary embodiment of the present invention, the sensor chip may include a solid molded body having at least one channel.

In one exemplary embodiment of the present invention, the sensor chip may include layers that may be bonded together thus rendering the chip usable in high pressure conditions. Further, the chip may be designed to be very thin and have a slim credit card look to it.

Various exemplary embodiments of the sensor chip and methods of manufacture are disclosed in commonly assigned U.S. Pat. Nos. 5,500,071, 5,658,413 and 6,033,628, all herein incorporated by reference in their entirety. The sensor chip may be modified from these references, however, in that it is required here that the chip be made from a non-transparent material that allows non-visible radiation, i.e., radiation outside the range of 390 nm (violet) to 780 nm (red), the visible range portion of the spectrum, produced by the SPR optical detector to pass through and interact with a surface plasmon generating layer in or on the chip.

A SPR system of an exemplary embodiment of the present invention includes a sensor substrate and an optical detector. The optical detector may be configured to generate non-visible radiation in a predetermined wavelength detection range and to direct said radiation towards the sensor substrate. At least a portion of the sensor substrate contains a surface plasmon generating film. The sensor substrate is made from a material that is not transparent to visible light but allows for penetration of the non-visible radiation to the surface plasmon generating film.

In an exemplary embodiment of the present invention, the substrate may include a sensor chip having at least one channel. At least a portion of the sensor chip in or adjacent the channel may contain the surface plasmon generating film.

In an exemplary embodiment of the present invention, the sensor chip may include affinity media connected to the surface plasmon generating film.

In an exemplary embodiment of the present invention, the sensor chip may have chromatographic media, e.g., chemically modified silica-based or 'gold-on-silica' based chromatographic media, in the channel adjacent to or downstream from the surface plasmon generating film in a separate channel or chamber. The media may be modified in an identical manner as the surface plasmon generating film. Modification may occur either in situ or prior to its placement in the channel or chamber. Modifications that occur in situ due to the contents of the flow stream may be ligand-ligate attachments that may be simultaneously executed with the section of the channel that contains or is in contact with the surface plasmon generating film. Chemical modifications that may occur prior to placement of the media within the channel or chamber may be of a similar, if not identical, process that has been executed on the surface plasmon generating film that enables the film to accept ligand-ligate attachments.

The media may be placed within the channel above the area where the SPR phenomenon is occurring or downstream in the channel or chamber in an area that is physically situated beyond the surface plasmon generating film. This area, channel or chamber may be created, for example, using a weir structure or by adjusting the area, channel or chamber dimensions, e.g., provide for a taper, so as to cause a congregation of media in one area.

In an exemplary embodiment of the present invention, the sensor chip or sensor substrate may be made from polyimide.

In an exemplary embodiment of the present invention, the optical detector may be configured to generate radiation having a wavelength greater than or equal to approximately 700 nm.

In an exemplary embodiment of the present invention, the sensor chip or sensor substrate may be made from silicon.

In an exemplary embodiment of the present invention, the optical detector may be configured to generate radiation having a wavelength greater than or equal to approximately 1100 nm.

In an exemplary embodiment of the present invention, the optical detector may include a detector configured to detect the radiation after it has reflected from the surface plasmon generating film.

In an exemplary embodiment of the present invention, the detector may be a silicon based detector, for example, such as one of a PIN diode, CMOS chip and a CCD array.

In an exemplary embodiment of the present invention, the detector may be an infrared photodetector.

In an exemplary embodiment of the present invention, the infrared photodetector may include an InGaAs sensor.

In an exemplary embodiment of the present invention, the SPR system may include a pump for pumping sample for analysis through the channel.

An exemplary embodiment of a sensor chip of the present invention may include a substrate, at least a portion of said substrate containing a surface plasmon generating film. The sensor chip may at least partially be made from a material that is not transparent to visible radiation but allows radiation having a predetermined wavelength in at least a portion of the non-visible wavelength range to pass through the sensor chip to the film.

In an exemplary embodiment of the present invention, the substrate may includes at least one channel and the surface plasmon generating film may be located in or adjacent said channel.

In an exemplary embodiment of the present invention, the substrate may include multiple layers adhered together.

In an exemplary embodiment of the present invention, the sensor chip or sensor substrate may include affinity media or chromatographic separation media connected to the surface plasmon generating film.

In an exemplary embodiment of the present invention, the substrate may be made from polyimide or silicon.

An exemplary method of the present invention includes steps for using a microfluidic system for SPR analysis. The microfluidic system may include a sensor chip and an optical detector. The sensor chip may include at least one channel, at least a portion of said channel containing a surface plasmon generating film. The optical detector may generate non-visible radiation in a predetermined wavelength detection range and may be configured to direct said radiation towards the sensor chip. The sensor chip may be made from a material that is not transparent but that allows radiation in the predetermined wavelength detection range to pass through to the surface plasmon generating film. The method may include passing a solution of interest through the channel and passing non-visible radiation generated by the optical detector through the sensor chip towards the surface plasmon generating film.

In an exemplary embodiment of the present invention the sensor chip may include an affinity media attached to the surface plasmon generating film.

In an exemplary embodiment of the present invention the sensor chip may include chromatographic separation media connected to the surface plasmon generating film.

In an exemplary embodiment of the present invention, the sensor chip may be made from polyimide and a lower value of the predetermined wavelength range may be 700 nm.

In an exemplary embodiment of the present invention, the sensor chip may be made from one of polyimide and silicon and a lower value of the predetermined wavelength range may be 1100 nm.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
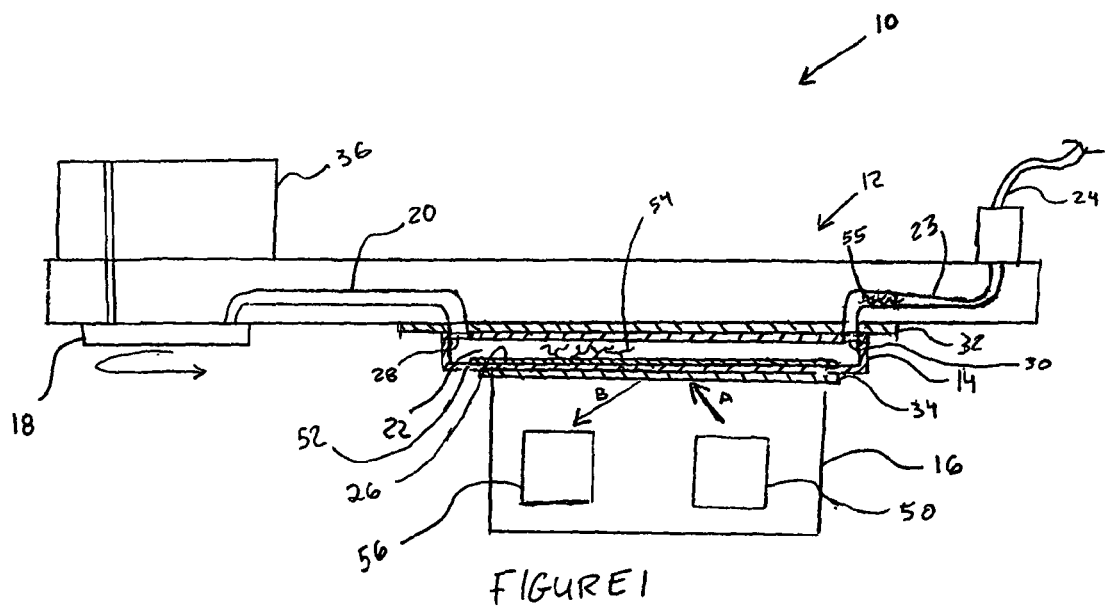
FIG. 1 is a longitudinal cross sectional view of the microfluidic system of the present invention.

FIG. 1 illustrates the microfluidic system 10 of an exemplary embodiment of the present invention. The microfluidic system 10 may include a pumping table 12, sensor chip 14 and an optical detector 16. A sample buffer may be pumped via a pumping mechanism, for example, a rotor 18, through a channel 20 in the pumping table 12 into a channel 22 in the sensor chip 14 via inlet 28 and back into pumping table 12 via outlet 30 where it may exit via waste line 24. A stator 36, including, for example, a six port rotary valve, may be connected to the pumping table 12 and used for input of sample and carrier buffers. The valve may also include a waste output, for example, for elimination of extra sample buffer.

Figure 2:
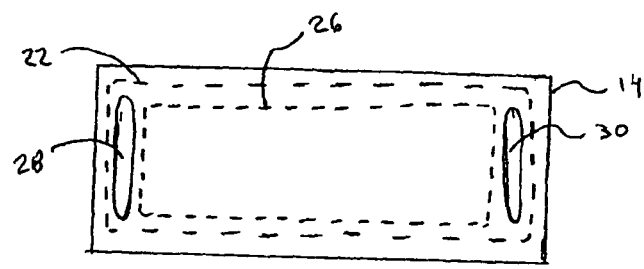
FIG. 2 is a top view of the sensor chip shown in cross section in FIG. 1.

FIG. 2 illustrates a top view of the sensor chip 14 shown in cross section in FIG. 1. The channel 22, shown in dashed lines, includes a surface plasmon generating film 26, also shown in dashed, which may be made from a surface plasmon generating materials, such as but not limited to a metal, such as gold or silver. The film 26 may coat the entire surface of the channel 22, including side walls, or may cover only a portion of the channel, i.e., a bottom wall portion 52.

Channel 22 may have a length in the range of approximately 5 μm to 200 μm, a depth in the range of approximately 5 μm to 200 μm, and a length in the range of approximately a few millimeters to 2.5 cm. Channel 22 is shown having a rectangular cross section but may also take on other shapes, e.g., circular, oval, etc. Further, inlet 28 and outlet 30 may take on alternate shapes as well.

Coupling covers 32 and 34, for example, made from glass, may be placed between the sensor chip 14 and the pumping table 12 and between the optical detector 16 and sensor chip 14, respectively. Further, a thin film coupling film (not shown) over the glass coupling cover 34 may also be used to assure intimate optical contact or coupling between the glass coupling cover 34 and the sensor chip 14. The thin film may be made from an index of refraction matching substance which matches the index of refraction of sensor chip 14 to the index of refraction of optical detector 16. The thin film may be made, for example, from polyimides, such as Upilex and Kapton products, and may have a thickness, for example, of approximately 10 to 150 μm.

In an exemplary embodiment of the present invention, as shown in FIGS. 1 and 2, the sensor chip 14 may be a solid molded unit including the channel 22 therein. The sensor chip 14 may include a plurality of separate or interconnected channels, not shown.

The choice of non-transparent materials for the chip sensor 14 may be test specific. Polyimides boast chemical resistance, low protein adsorption and fast prototyping and integration. Silicon sensors are useful because they allow for an integration of electronic circuits and use of known photolithography and micromachining techniques.

It has been demonstrated that polyimides exhibit low sorptive properties towards proteins and peptides, which are known to be particularly difficult to analyze in prior silicon dioxide-based separation systems. Successful demonstrations of separations with this difficult class of solutes typically ensures that separation of other classes of solutes will be not be problematic. Further, since polyimide is a condensation polymer, it is possible to chemically bond groups to the surface, which can provide a variety of desirable surface properties, depending on the target analysis. These bonds to the polymeric substrate demonstrate pH stability in the basic region (pH 9-10).

Sensor chip 14 may allow radiation produced by a radiation generator 50 of the optical detector 16 to pass through so as to generate the surface plasmon. The sensor chip 14 is non-transparent but may be made from a material which allows radiation produced by the radiation generator 50 of the optical detector 16, for example, along arrow A, to pass through the bottom portion 52 of the sensor chip 14 and reflect back to a radiation sensor 56 of the optical detector 16, for example, along arrow B.

In an exemplary embodiment of the present invention, the sensor chip 14 may be made from a polyimide material, such as those available under the trademarks Kapton®, from Dupont (Wilmington, Del.), or Upilex® from Ube Industries, Ltd. (Japan). Polyimide is relatively transparent for wavelengths longer than or equal to 700 nm. Therefore, in an exemplary embodiment of the present invention using a polyimide sensor chip, for example, radiation generator 50 of optical detector 16 is configured so as to emit radiation of 700 nm or greater for detection purposes.

Silicon and polyimide materials are relatively transparent for wavelengths longer than 1100 nm. Therefore, for embodiments incorporating either polyimide or silicon sensor chips, for example, the radiation generator 50 of optical detector 16 may be configured to emit, for example, radiation with a wavelength of 1100 nm or greater. The radiation may pass through at least a portion of the sensor chip 14 made from silicon and/or polyimide and may generate a detectable surface plasmon.

The SPR system of the present invention may be used in the following exemplary manner. First, a determination may be made as to which sensor chip material type is best suited for the particular type of required testing to be done. Unlike prior art SPR systems, the sensor chip 14 need not be transparent as the optical detector 14 is configured to emit radiation which passes through a non-transparent material so as to generate the surface plasmon. As indicated above, polyimide boasts chemical resistance, low protein adsorption and fast prototyping and integration. Further, silicon sensors are useful because they allow for an integration of electronic circuits and for the use of known photolithographic and micromachining techniques. Either of these materials may be used for the sensor chip 14 despite the fact that they are not transparent.

At least a portion of channel 22 in the preselected sensor chip 14 may be treated with media 54, e.g., chemically treated silica-based media, gold based media, non-specific binding polymers, hydrophobic siloxane surfaces, ion-exchange polymers, etc., which may be attached, for example, directly to the film 26 or indirectly via a high surface area media, such as nano-beads, a nanoporous coating, etc.

In an example embodiment of the present invention, chromatographic media 55, e.g., chemically modified silica-based or 'gold-on-silica' based chromatographic media, may be connected to the surface plasmon generating film 26 in the channel 22 or, as shown in FIG. 1, downstream from the surface plasmon generating film in a separate channel or chamber 23. The media may be modified in an identical manner as the surface plasmon generating film 26. Modification may occur either in situ or prior to its placement in the channel or chamber 22,23. Modifications that occur in situ due to the contents of the flow stream may be ligand-ligate attachments that may be simultaneously executed with the section of the channel 22 that contains or is in contact with the surface plasmon generating film. Chemical modifications that may occur prior to placement of the media within the channel or chamber 23 may be of a similar, if not identical, process that has been executed on the surface plasmon generating film that enables the film to accept ligand-ligate attachments.

The media 55 may be placed within the channel 22 above the area where the SPR phenomenon is occurring or downstream in the channel or chamber 23 in an area that is physically situated beyond the surface plasmon generating film. This area, channel or chamber 23 may be created, for example, using a weir structure or, as shown in FIG. 1, by adjusting the area, channel or chamber dimensions, e.g., provide for a taper, so as to cause a congregation of media in one area.

In an exemplary embodiment of the present invention, SAM (self-assembled monolayer) or carboxylated polymer brush including, for example, carboxylated dextran, polyglutamic acid, poly-acrylic acid, or mercaptoundecanoic acid, etc. covalently linked to immunoglobulins (IgG's), using, for example, amine-functional groups on the IgG's, may be attached to a channel surface.

In an exemplary embodiment of the present invention, a hydrophobic surface may be used which denatures and binds biotin-labeled bovine serum albumin (biotin-BSA), which in turn can be used to immobilize avidin or streptavidin molecules, which in turn can be used to immobilize biotin-modified (or "conjugated") IgG's.

An unknown sample or ligate solution, including, for example, proteins or peptide factions, may be introduced into the channel 22, for example, via rotor 18 and stator 36, to contact the media 54. In an exemplary embodiment, a protein A having an affinity for IgG's may be used. The protein A may be immobilized by electrostatic interactions on a poly(lysine) or poly(allylamine) modified substrate (polycationinc) or by covalent attachment via amine-carboxylate chemistry, or by reduced amination using aldehyde-rich surfaces, e.g., an aldehyde dextran brush.

The interaction between the media 54 and unknown sample or ligate may be observed by directing radiation produced by the radiation generator 50 of the optical detector 16 towards a bottom surface of the film 26 and using a processing unit (not shown) to calculate a change in the "resonance angle." The "resonance angle" may be determined using known methods, for example, the sensor chip 14 or the optical detector 16 may be rocked or pivoted, in which case the resonant condition is detected as a dip in the reflection intensity as a function of the wavelength of illumination, or a broad band radiation output by the optical detector 16 may be scanned or swept, in which case a spectrometer may be used to find the wavelength at which the reflected light gets absorbed by the resonance.

As indicated above, the radiation produced by the optical detector 16 may include at least radiation outside the visible range portion of the spectrum.

Further, as indicated above, optical detector 14 may also include sensor 56 for measuring the radiation reflected from the film 26. In an exemplary embodiment of the invention, the sensor 56 may be a silicon based sensor, e.g., a CMOS chip, PIN diode, CCD array, etc.

Wavelengths above approximately 900 nm tend to pass through a silicon sensor, i.e., silicon based sensors are transparent to higher wavelengths. Therefore, in one exemplary embodiment of the present invention, the sensor 56 may be an infrared sensor, such as, an InGaAs sensor, for example, an InGaAs sensor produced by Hamamatsu. Infrared sensors are sensitive to radiation between approximately 1100 and 2000 nm.

It is noted that the present invention is not limited to microfluidic chips. Rather the sensor chip may comprise a substrate, with or without channels, made from a non-transparent material, e.g., polyimide or silicon, having a plasmon generating film. In which case, the sensor chip 14 may be simple solid substrate mounted or placed above an optical detector. A sample to be analyzed may be placed on a top surface of the substrate above a surface plasmon generating layer.

Figure 3:
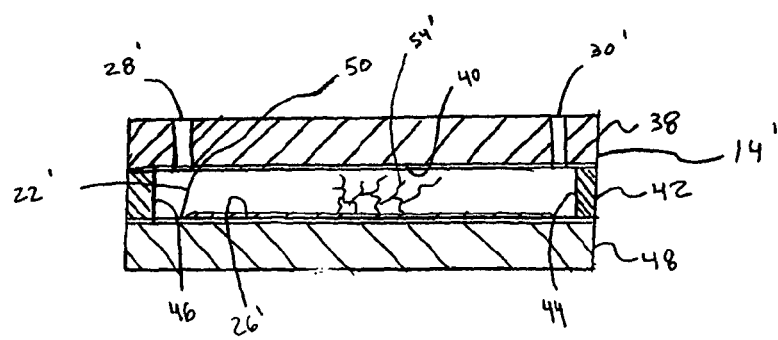
FIG. 3 is a cross sectional view of an exemplary embodiment of a sensor chip of the present invention.

FIG. 3 illustrates a cross section of a sensor chip 14' of another exemplary embodiment of the present invention. The sensor chip 14' may include a multi-layered substrate including a top layer 38, having a top channel surface 40, a middle layer 42, having a first side channel surface 44 and a second side channel surface 46, and a bottom layer 48, having a bottom channel surface 50. All the layers 38, 42 and 48 may be permanently bonded together on their respective top and bottom surfaces to form the sensor chip 14'. The top channel surface 40, first side channel surface 44, second side channel surface 46 and bottom channel surface 50 together define channel 22'. Channel 22' may be laser ablated or etched in middle layer 42 and may have a length in the range of approximately 5 μm to 200 μm, a depth in the range of approximately 5 μm to 200 μm, and a length in the range of approximately a few millimeters to 2.5 cm. Channel 22' is shown having a rectangular cross section but may also take on other shapes, e.g., circular, oval, etc. Further, inlet 28' and outlet 30' to channel 22' may take on alternate shapes as well.

Note that sensor chip 14' may comprise two layers or more than three layers. If consisting of only two layers channel 22' may be created by recesses formed in surfaces of one or both of the layers. Alternatively, multiple layers may be used to either increase the thickness of a given level or to, in effect, stack recess containing levels. In an exemplary embodiment of the invention, two sensor chips may be stacked to form a double sensor chip.

Layers 38, 42, 48 may be made from the same or different materials and may be co-extruded with a thin layer of a thermal adhesive form of polyimide known as KJ®, available from Dupont, used to join layers 38, 42, 48 together. The thermal adhesive layer can be on one or both sides of the layers 38, 42, 48.

A surface plasmon generating film 26' may coat at least a portion of bottom channel surface 50. The first side channel surface 44, the second side channel surface 46 and/or the top surface 40 may also be coated with film 26'. Film 26' may be made from a surface plasmon generating material, such as but not limited to metal, such as gold or silver. In one example embodiment of the present invention, the coating is made from a metal having a thickness, for example, on the order of between 20 and 50 nanometers.

Layers 38, 42, 48 may be made from a material that have sufficient strength and flexibility at thicknesses in the range of 10 microns to 1 millimeter. The material may also be solvent resistant.

In an exemplary embodiment of the invention, as with the sensor chip 14 of FIGS. 1 and 2, film 26' may be treated with media 54 and may include chromatographic media 55 in the channel 22' or downstream from the surface plasmon generating film 26' in a separate channel or chamber, as shown in FIG. 1.

As many apparently widely different embodiments of the present invention can be made without departing from the spirit and scope thereof, it is to be understood that the invention is not limited to the specific embodiments thereof except as defined in the appended claims.

What is claimed is:

1. A SPR system, comprising:
   a sensor chip comprising a sensor substrate, a channel, an upper channel surface, a lower channel surface and a side channel surface;
   and an optical detector, said optical detector configured to generate non-visible radiation in a predetermined wavelength detection range and to direct said radiation towards the sensor substrate, wherein the channel contains a surface plasmon generating film, the sensor substrate comprising a material that is not transparent to visible light but is substantially transparent to non-visible radiation.

2. The SPR system of claim 1, wherein at least a portion of the sensor chip in or adjacent the channel contains the surface plasmon generating film.

3. The SPR system of claim 1, further comprising affinity media connected to the surface plasmon generating film.

4. The SPR system of claim 1, further comprising chromatographic separation media at least one of (i) adjacent the surface plasmon generating film and (ii) downstream from the surface plasmon generating film.

5. The SPR system of claim 1, wherein the sensor substrate is made from polyimide.

6. The SPR system of claim 5, wherein the optical detector is configured to generate radiation having a wavelength greater than or equal to approximately 700 nm.

7. The SPR system of claim 1, wherein the sensor substrate is made from silicon.

8. The SPR system of claim 7, wherein the optical detector is configured to generate radiation having a wavelength greater than or equal to approximately 1100 nm.

9. The SPR system of claim 1, wherein the optical detector further includes a detector configured to detect the radiation after it has reflected from the surface plasmon generating film.

10. The SPR system of claim 9, wherein the detector is a silicon based detector.

11. The SPR system of claim 10, wherein the silicon based detector includes one of a PIN diode, CMOS chip and a CCD array.

12. The SPR system of claim 9, wherein the detector is an infrared photodetector.

13. The SPR system of claim 12, wherein the infrared photodetector comprises an InGaAs sensor.

14. The SPR system of claim 2, further including a pump for pumping sample for analysis through the channel.

15. A sensor chip, comprising:
    a channel comprising a substrate, an upper channel surface, a lower channel surface and a side channel surface, wherein said channel contains a surface plasmon generating film, and the substrate comprising a material that is not transparent to visible radiation but is substantially transparent to radiation having a predetermined wavelength in at least a portion of the non-visible wavelength range.

16. The sensor chip of claim 15, wherein the substrate includes at least one channel and the surface plasmon generating film is located in or adjacent said channel.

17. The sensor chip of claim 15, wherein the substrate includes multiple layers adhered together.

18. The sensor chip of claim 15, further comprising affinity media connected to the surface plasmon generating film.

19. The sensor chip of claim 16, further comprising chromatographic separation media in the at least one channel connected to the surface plasmon generating film.

20. The sensor chip of claim 15, wherein the substrate is made from polyimide.

21. The sensor chip of claim 15, wherein the substrate is made from silicon.

22. A method for using a microfluidic system for SPR analysis, said microfluidic system comprising a sensor chip and an optical detector, said sensor chip comprising a channel, an upper channel surface, a lower channel surface and a side channel surface, wherein the channel contains a surface plasmon generating film, said optical detector generating non-visible radiation in a predetermined wavelength detection range and being configured to direct said radiation towards the sensor chip, the sensor chip being made from a material that is not transparent but allowing radiation in the predetermined wavelength detection range to pass through to the surface plasmon generating film, said method comprising:
    passing a solution of interest through the channel; and
    passing non-visible radiation generated by the optical detector through the sensor chip towards the surface plasmon generating film.

23. The method of claim 22, wherein the sensor chip includes an affinity media attached to the surface plasmon generating film.

24. The method of claim 22, wherein the sensor chip includes chromatographic separation media connected to the surface plasmon generating film.

25. The method of claim 22, wherein the sensor chip is made from polyimide and a lower value of the predetermined wavelength range is 700 nm.

26. The method of claim 22, wherein the sensor chip is made from one of polyimide and silicon and a lower value of the predetermined wavelength range is 1100 nm.

\* \* \* \* \*